United States Patent [19]

Ishida et al.

[11] 4,055,716
[45] Oct. 25, 1977

[54] N⁴-ACYL-1-ARABINOFURANOSYLCYTO-SINE-5'-ESTERS

[75] Inventors: Torao Ishida; Takashi Shirai; Minoru Akiyama, all of Fuji, Japan

[73] Assignee: Asahi Kasei Kogyo Kabushiki Kaisha, Osaka, Japan

[21] Appl. No.: 675,050

[22] Filed: Apr. 8, 1976

[30] Foreign Application Priority Data

Apr. 8, 1975  Japan .................................. 50-41815
Apr. 8, 1975  Japan .................................. 50-41816

[51] Int. Cl.² ............................................. C07H 19/06
[52] U.S. Cl. ...................................... 536/23; 424/180
[58] Field of Search .................. 536/23, 22, 29, 27

[56] References Cited

U.S. PATENT DOCUMENTS 3,457,253  7/1969  Wechter .................................. 536/27
3,847,898  11/1974  Kelly et al. ............................. 536/23

*Primary Examiner*—Johnnie R. Brown

*Attorney, Agent, or Firm*—Sughrue, Rothwell, Mion, Zinn and Macpeak

[57] ABSTRACT $N^4$-Acyl-1-$\beta$-D-arabinofuranosylcytosine-5'-esters represented by the formula

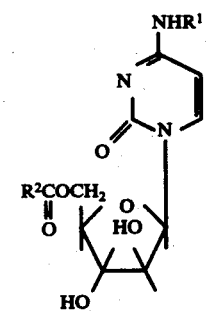

wherein $R^1$ represents an acyl group having 3 to 28 carbon atoms and $R^2$ represents an $XCH_2$, $XCH_2CH_2$ or $CH_3CHX$ group, wherein X represents a halogen atom, a $(CH_3)_2N$ or $(C_2H_5)_2N$ group.

5 Claims, 5 Drawing Figures

N4ACYL-1-ARABINOFURANOSYLCYTOSINE-5'-ESTERS

BACKGROUND OF THE INVENTION

1. Field of the Invention

This invention relates to N4-acyl-1-β-D-arabinofuranosylcytosine-5'-amino esters having antileukemial activity and N4-acyl-1-β-D-arabinofuranosylcytosine-5'-haloesters which are intermediates in the synthesis of the above-described arabinosuranosylcytosine amino esters.

2. Description of the Prior Art

N4-Acyl-1-β-D-arabinofuranosylcytosines have a remarkable effect aginst L-1210 leukemia in mice, and, among them, those carrying an acyl group having 14 to 22 carbon atoms exhibit particularly remarkable effects.

These N4-acyl-1-β-D-arabinofuranosylcytosines are generally insoluble or only slightly soluble in water, and can be prepared by reacting arabinofuranosylcytosine and an acid anhydride in water and a water-miscible organic solvent, for example, a mixed solvent of water-dioxane (1:10 by volume), at a temperature of about 60° C for about 4 hours.

SUMMARY OF THE INVENTION

An object of this invention is to provide compounds which exhibit excellent dispersibility in water by chemically modifying N4-acyl-1-β-D-arabinofuranosylcytosines.

The inventors performed various investigations to discover more effective antileukemial agents by selecting materials which would prolong the life of mice infected by L-1210 leukemia, using the method developed by the Drug Research & Development Department of the National Cancer Institute of the United States for screening antitumour agents and antileukemial agents for humans (it has been confirmed from data collected on a world-wide basis that medicaments effective against L-1210 leukemia have the greatest possibility of being effectively used for the treatment of leukemia in humans) and, as a result, the inventors found that novel compounds, N4-acyl-1-β-D-arabinofuranosylcytosine-5'-amino esters, meet the above described object, and also discovered novel N4-acyl-1-β-D-arabinofuranosylcytosine-5'-haloesters which are useful as intermediates therefor.

BRIEF DESCRIPTION OF THE ACCOMPANYING DRAWINGS

DETAILED DESCRIPTION OF THE INVENTION

Figure 1:
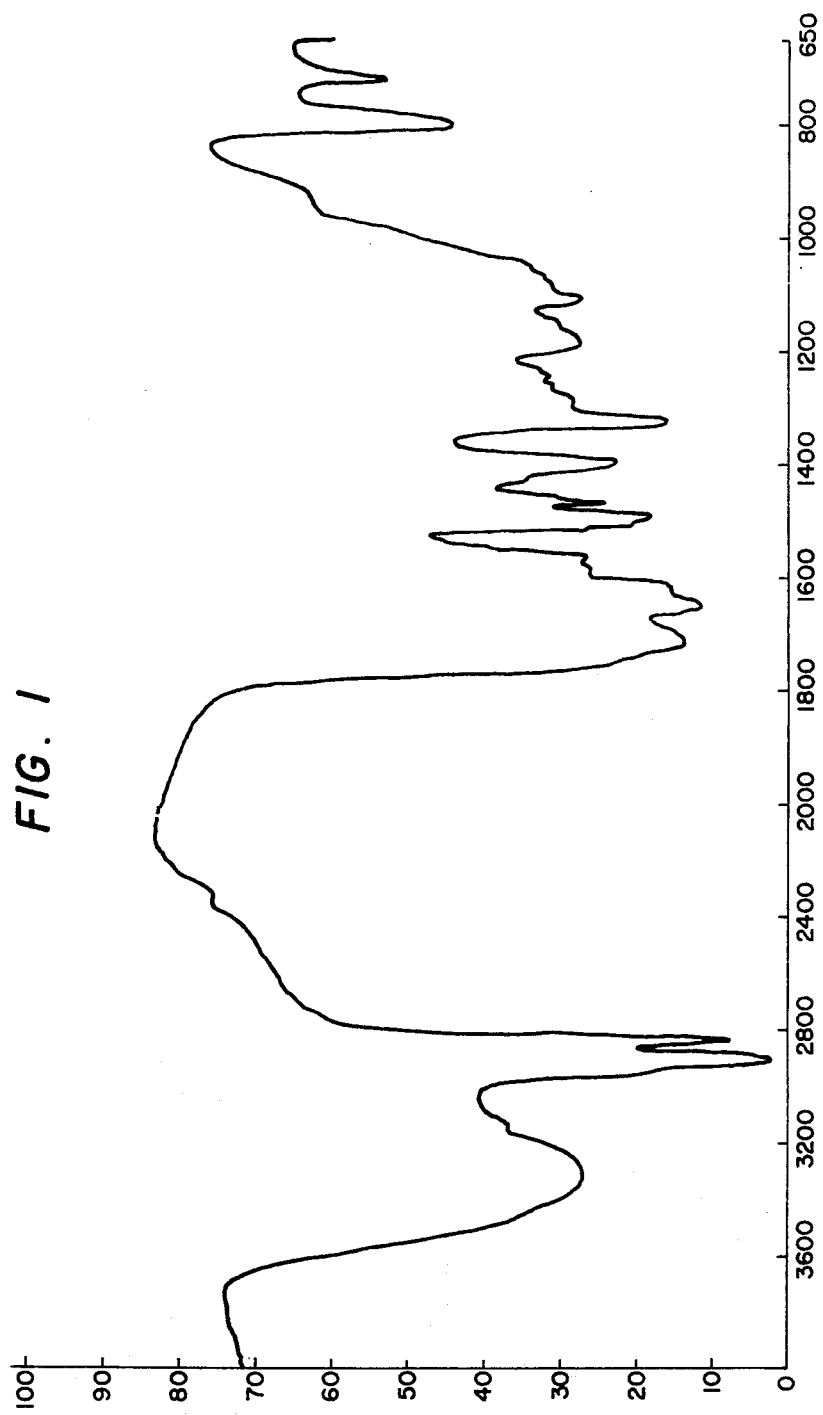
FIG. 1 shows the infrared absorption spectrum of N4-stearoyl-1-β-D-arabinofuranosylcytosine-5'-chloroacetate according to the present invention.
Figure 2:
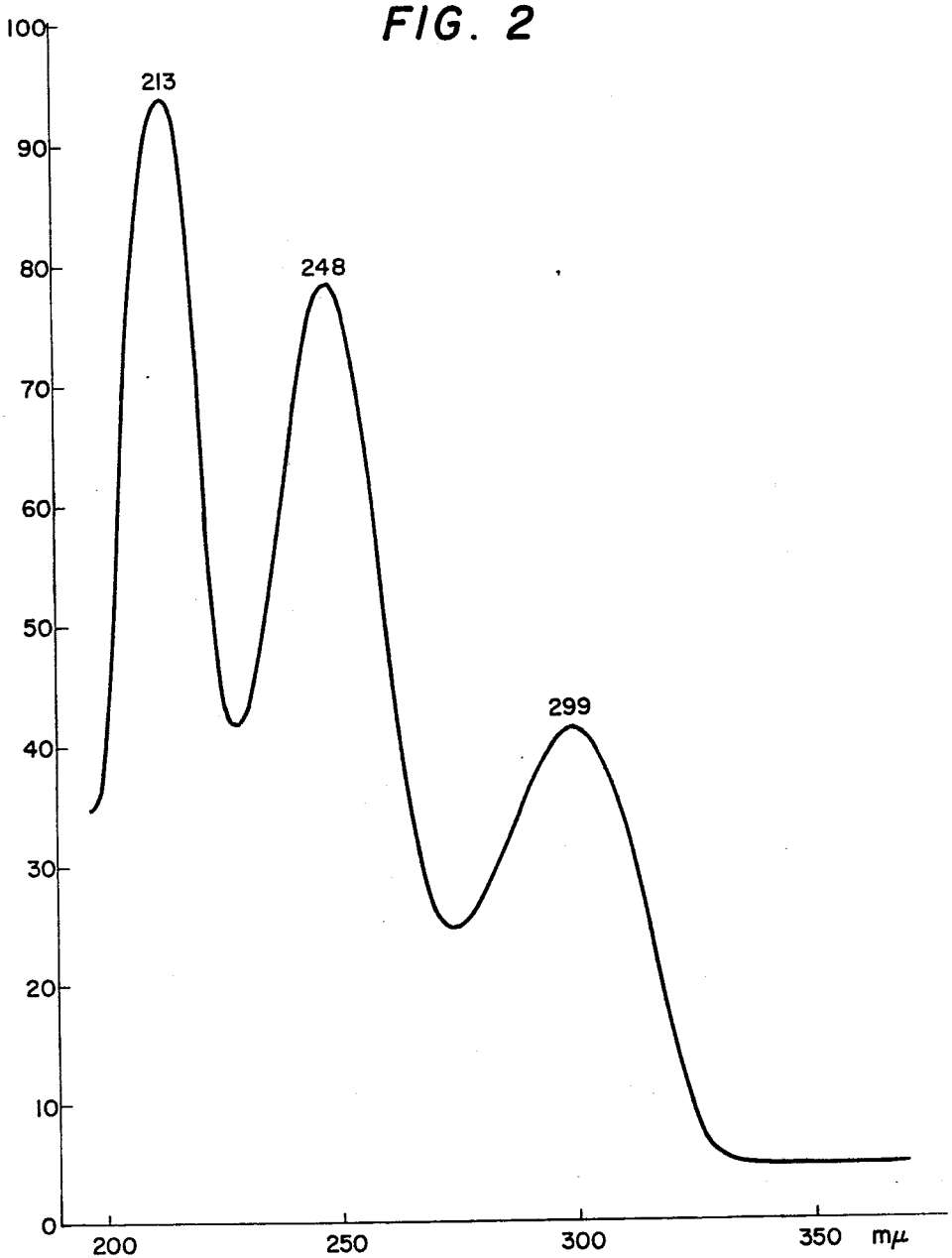
FIG. 2 shows the ultraviolet absorption spectrum of a solution of N4-palmitoyl-1-β-D-arabinofuranosylcytosine-5'-chloropropionate in methanol according to the present invention.
Figure 3:
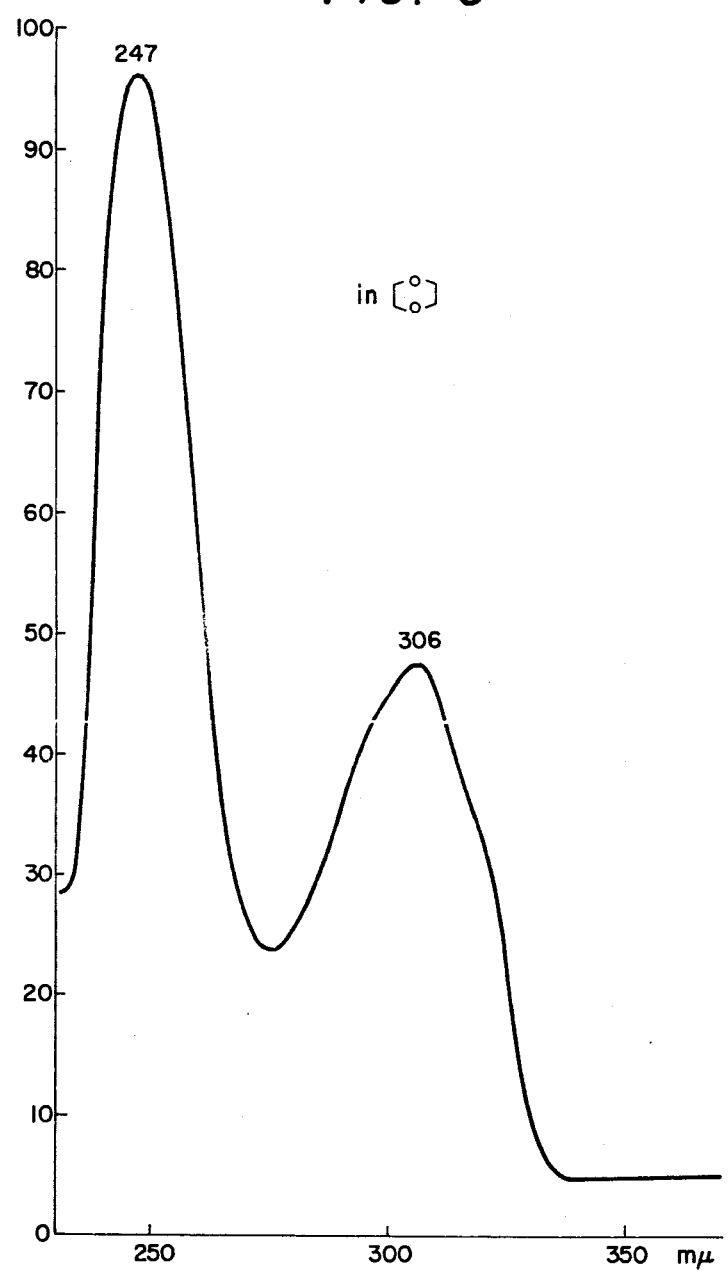
FIG. 3 shows the ultraviolet absorption spectrum of a dioxane solution of N4-margaroyl-1-β-D-arabinofuranosylcytosine-5'-N,N-diethylglycinate according to the present invention.
Figure 4:
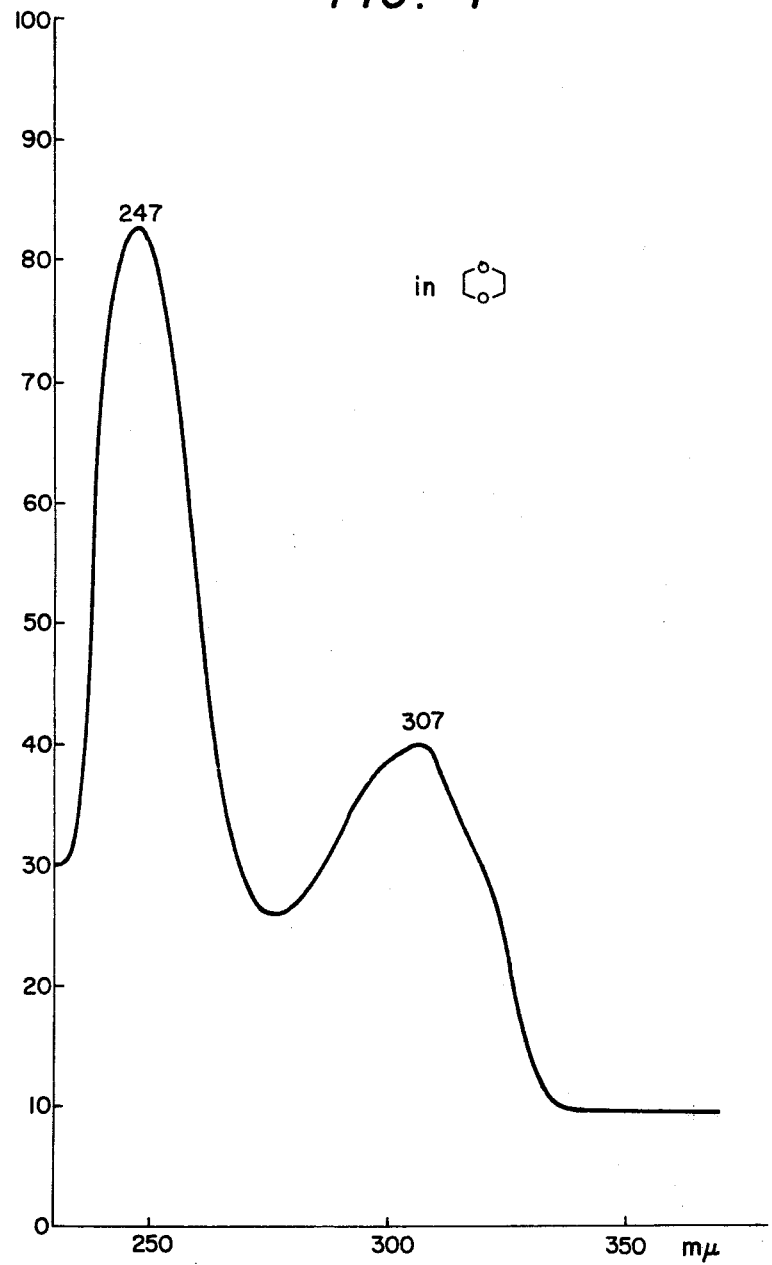
FIG. 4 shows the ultraviolet absorption spectrum of a dioxane solution of N4-stearoyl-1-β-D-arabinofuranosylcytosine-5'-N,N-diethylaminopropionate according to the present invention.
Figure 5:
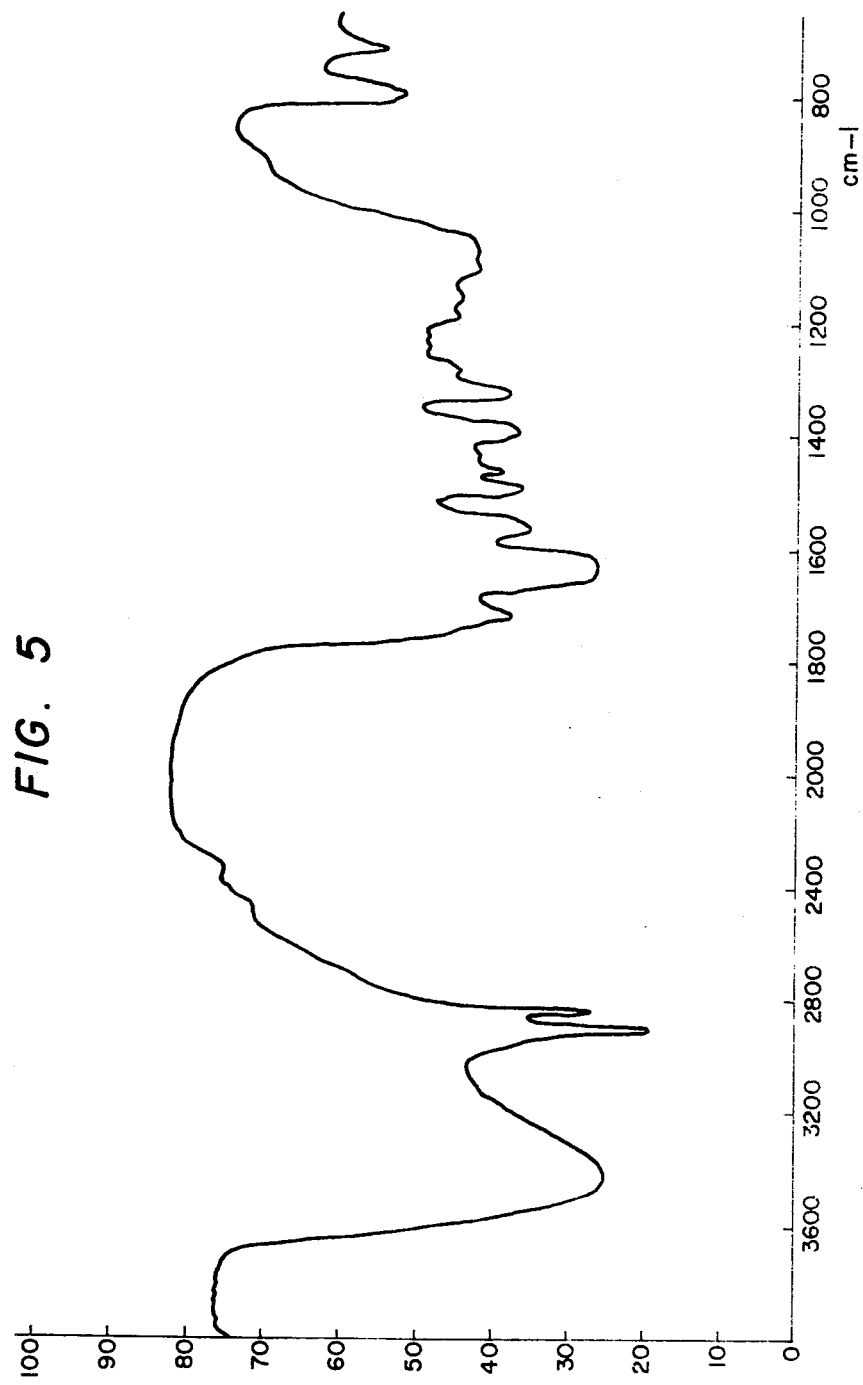
FIG. 5 shows the infrared absorption spectrum of N4-stearoyl-1-β-D-arabinofuranosylcytosine-5'-N,N-diethylaminopropionate according to the present invention.

The N4-acyl-1-β-D-arabinofuranosylcytosine-5'-esters present invention can be represented by the formula (I)

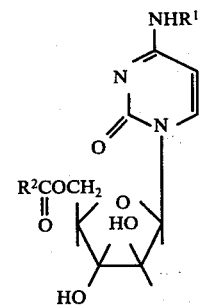

wherein $R^1$ represents an acyl group having 3 to 28 carbon atoms, preferably an acyl group selected from the class consisting of propionyl, butyryl, iso-butyryl n-valeryl, isovaleryl, caproyl, heptanoyl, caprylyl, nonanoyl, capryl, undecanoyl, lauroyl, tridecanoyl, myristoyl, tetradecenoyl, pentadecanoyl, palmitoyl, margaroyl, stearoyl, oleoyl, nonadecanoyl, arachidoyl, heneicosanoyl, behenoyl and lignoceroyl, most preferably an acyl group selected from the class consisting of myristoyl, tetradecenoyl, pentadecanoyl, palmitoyl, margaroyl, stearoyl, oleoyl, nonadecanoyl, arachidoyl, heneicosanoyl and behenoyl; and $R^2$ represents an $XCH_2$, $XCH_2CH_2$ or $CH_3CHX$ group wherein X represents a halogen atom, preferably a halogen atom selected from the class consisting of chlorine and bromine, or X represents a $(CH_3)_2N$ or $(C_2H_5)_2N$ group. The N4-acyl-1-β-D-arabinofuranosylcytosine-5'-haloesters represented by formula (I), wherein X represents a halogen atom, can be used as intermediates for forming the N4-acyl-1-β-D-arabinofuranosylcytosine-5'-aminoesters represented by formula (I), wherein X represents a $(CH_3)_2N$ or $(C_2H_5)_2N$ group.

N4-Acetyl-1-β-D-arabinofuranosylcytosines of formula (I) wherein $R^1$ has 2 carbon atoms are not included in this invention since the acetyl group is easily released during the working-up procedures after reaction.

The N4-acyl-1-β-D-arabinofuranosylcytosine-5'-haloacetates and N4-acyl-1-β-D-arabinofuranosylcytosine-5'-halopropionates according to the present invention can be obtained by reacting an N4-acyl-1-β-D-arabinofuranosylcytosine with a haloacetyl halide and a halopropionyl halide, respectively. The halide is advantageously used in an equimolar amount to about 3 molar times bases on the starting material. The halide may be added all at once, but is particularly advantageously added in portions over the reaction in order to increase the yield of the product.

The reaction pressure is, in general, atmospheric pressure. The reaction temperature is not particularly limited, but generally low temperatures (from room temperature to less than about 50° C) are desirable. The reaction time is preferably more than about 6 hours and up to about 24 hours. It is advantageous to carry out the reaction in an organic solvent of high polarity, for example, pyridine, acetone, tetrahydrofuran, N,N-dimethylformamide, N,N-dimethylacetamide and the like, preferably N,N-dimethylacetamide.

The progress of the esterification can be followed by thin layer chromatography using silica gel and a mixed solvent of chloroform:methanol (e.g., about 5:1 by volume). After completion of the reaction, any unreacted acid halide can be decomposed with water, thereby precipitating the reaction product. The resulting product can be subjected to the subsequent reaction without purification. However, if necessary, purification can be conducted by recrystallization, column chromatography or the like. Acetone, tetrahydrofuran, ethyl acetate and the like are used as a solvent for recrystallization. In the case of column chromatography, silica gel and a mixed solvent of methanol:chloroform are used as an adsorbent and a developer, respectively, and the mixing ratio of the methanol:chloroform developer is varied initially from about 1:20, gradually increasing the volume of methanol, finally to about 1:5.

The reaction product can be identified by its infrared absorption spectrum, ultraviolet absorption spectrum and by elementary analysis.

The $N^4$-acyl-1-$\beta$-D-arabinofuranosylcytosine-5'-amino esters represented by formula (I) wherein X represents a $(CH_3)_2N$ or $(C_2H_5)_2N$ group can be prepared by reacting the above described $N^4$-acyl-1-$\beta$-D-arabinofuranosylcytosine-5'-haloester with dimethylamine or diethylamine in an amount of about 1 to about 10 moles per one mole of the $N^4$-acyl-1-$\beta$-D-arabinofuranoylcytosine-5'-haloester used. The reaction temperature is not particularly limited, but generally low temperatures (from room temperature to below 0° C) are desirable. The reaction time ranges from about more than about 5 minutes to about 24 hours, preferably 4 to 5 hours, at atmospheric pressure. The reaction may be conducted without any solvent or in a solvent such as diethyl ether, tetrahydrofuran, acetone, benzene, n-hexane, chloroform, methylene dichloride, etc., in an amount of about 1 to about 50 moles per one mole of dimethylamine or diethylamine used.

The above reaction may be effected in air, but is advantageously conducted under an atmosphere of argon or nitrogen because the working-up procedures are simpler.

The progress of the amination can be traced by thin layer chromatography using silica gel and a mixed solvent of chloroform:methanol (e.g., about 5:1 by volume). Confirming that the starting material has disappeared, the resulting amine hydrochloride is filtered, and the solvent and the unreacted amine are distilled off under reduced pressure. The white powder thus obtained is then purified by column chromatography using silica gel. As a developer, a mixed solvent of methanol:chloroform is employed varying the mixing ratio thereof initially from about 1:20 by gradually increasing the volume of methanol to a final value of about 1:5 by volume.

The reaction product thus obtained can be identified by its infrared absorption spectrum, ultraviolet absorption spectrum and nuclear resonance absorption spectrum and by elementary analysis.

The present invention will now be illustrated in more detail by several non-limiting examples. All processings are at atmospheric pressure, unless otherwise indicated.

EXAMPLE 1

1.01 g of $N^4$-stearoyl-1-$\beta$-D-arabinofuranosylcytosine was dissolved in 12 ml of N,N-dimethylacetamide, and a solution of 0.24 g of chloroacetyl chloride in N,N-dimethylacetamide was added thereto while on an ice-water bath followed by stirring for 1 hour at room temperature. To the mixture was further added 0.24 g of chloroacetyl chloride followed by stirring for 20 to 40 minutes at room temperature, and thereafter 100 ml of water was added to the resulting mixture to terminate the reaction. The precipitate thus formed was filtered, thoroughly washed with water and recrystallized from acetone. After drying in vacuo, i.e., 5 mmHg, 1.0 g of the product was obtained as a white amorphous solid in a yield of 94 mole%.

In the above reaction, it should be noted that the reaction should be completed in 20 to 40 minutes after the second addition of chloroacetyl chloride. If the reaction is terminated before the above recited time, the starting material, $N^4$-stearoyl-1-$\beta$-D-arabinofuranosylcytosine, would remain unreacted. On the other hand, if the reaction is continued for more than 40 minutes, the esterification would also proceed at the 3'-position. Therefore, as long as the reaction is stopped within the above recited time range, the desired product wherein only the 5'-position is selectively esterified can be obtained at high yield.

Elementary analysis for $C_{29}H_{48}O_7N_3Cl$: Calcd. (%): C, 59.42; H, 8.25; O, 19.11; N, 7.17; Cl, 6.05. Found (%): C, 59.52; H, 8.20; O, 19.08; N, 7.22; Cl, 6.00.

Ultraviolet absorption spectrum (methanol): $\lambda_{max}$: 213 m$\mu$, 248 m$\mu$ and 299 m$\mu$ Infrared absorption spectrum (KBr): 1733 cm$^{-1}$ (ester)

EXAMPLE 2

Following the same procedures as described in Example 1 except for varying the starting materials, the following $N^4$-acyl-1-$\beta$-D-arabinofuranosylcytosine-5'-haloesters were prepared:

$N^4$-Palmitoyl-1-$\beta$-D-arabinofuranosylcytosine-5'-chloroacetate:

Elementary analysis for $C_{27}H_{44}O_7N_3Cl$: Calcd. (%): C, 58.10; H, 7.95; O, 20.07, N, 7.53, Cl, 6.35. Found (%): C, 58.22, H, 7.98, O, 20.02, N, 7.50, Cl 6.32.

Ultraviolet absorption spectrum (methanol): $\lambda_{max}$: 213 m$\mu$, 248 m$\mu$ and 299 m$\mu$ $N^4$-Margaroyl-1-$\beta$-D-arabinofuranosylcytosine-5'-chloroacetate:

Elementary analysis for $C_{28}H_{46}O_7N_3Cl$: Calcd. (%): C, 58.79; H, 8.10; O, 19.57; N, 7.34; Cl 6.20. Found (%): C, 58.91; H, 8.05; O, 19.42; N, 7.41; Cl 6.23.

Ultraviolet absorption spectrum (methanol): $\lambda_{max}$: 213 m$\mu$, 248 m$\mu$ and 299 m$\mu$.

$N^4$-Propionyl-1-$\beta$-D-arabinofuranosylcytosine-5'-chloroacetate.

$N^4$-Butyryl-1-$\beta$-D-arabinofuranosylcytosine-5'-chloroacetate.

$N^4$-Valeryl-1-$\beta$-D-arabinofuranosylcytosine-5'-chloroacetate.

$N^4$-Caproyl-1-$\beta$-D-arabinofuranosylcytosine-5'-chloroacetate. $N^4$-Heptanoyl-1-$\beta$-D-arabinofuranosylcytosine-5'-chloroacetate.

$N^4$-Caprylyl-1-$\beta$-D-arabinofuranosylcytosine-5'-chloroacetate.

$N^4$-Lauroyl-1-$\beta$-D-arabinofuranosylcytosine-5'-chloroacetate.

$N^4$-Myristoyl-1-$\beta$-D-arabinofuranosylcytosine-5'-chloroacetate.

$N^4$-Tetradecenoyl-1-$\beta$-D-arabinofuranosylcytosine-5'-chloroacetate.

N[4]-Pentadecanoyl-1-β-D-arabinofuranosylcytosine-5'-chloroacetate.

N[4]-Nonadecanoyl-1-β-D-arabinofuranosylcytosine-5'-chloroacetate.

N[4]-Arachidoyl-1-β-D-arabinofuranosylcytosine-5'-chloroacetate.

N[4]-Behenoyl-1-β-D-arabinofuranosylcytosine-5'-chloroacetate.

N[4]-Lignoceroyl-1-β-D-arabinofuranosylcytosine-5'-chloroacetate.

EXAMPLE 3

1.01 g of N[4]-stearoyl-1-β-D-arabinofuranosylcytosine was dissolved in 12 ml of N,N-dimethylacetamide, and 0.27 g of β-chloropropionyl chloride was added to the solution while ice-cooling, followed by stirring while ice-cooling for 2 hours. 0.27 g of β-chloropropionyl chloride was additionally added to the resulting mixture followed by stirring while ice-cooling for 2 hours, and thereafter water was added to the reaction system to terminate the reaction. The precipitate formed was filtered, washed with water and then recrystallized from acetone. After drying in vacuo, i.e. 5 mmHg, 1.10 g of the product was obtained as a white amorphous solid in a yield of 93 mole%.

Elementary analysis for $C_{30}H_{50}O_7N_3Cl$: Calcd. (%): C, 60.03; H, 8.40; O, 18.66; N, 7.00; Cl, 5.91. Found (%): C, 60.00; H, 8.38; O, 19.80; N, 7.10; Cl, 6.00.

Ultraviolet absorption spectrum (methanol): $\lambda_{max}$: 213 mμ, 248 mμ and 299 mμ

Infrared absorption spectrum: 1733 cm$^{-1}$ (ester).

EXAMPLE 4

Following the same procedures as described in Example 3 except for varying the starting materials, the following N[4]-acyl-1-β-D-arabinofuranosylcytosine-5'-haloesters were prepared:

N[4]-Palmitoyl-1-β-D-arabinofuranosylcytosine-5'-chloropropionate:

Elementary analysis for $C_{28}H_{46}O_7N_3Cl$: Calcd. (%): C, 58.79; H, 8.10; O, 19.57; N, 7.34; Cl, 6.20. Found (%): C, 58.90; H, 8.07; O, 19.38; N, 7.42; Cl, 6.22.

Ultraviolet absorption spectrum (methanol): $\lambda_{max}$: 213 mμ, 248 mμ and 299 mμ

N[4]-Margaroyl-1-β-D-arabinofuranosylcytosine-5'-chloropropionate:

Elementary analysis for $C_{29}H_{48}O_7N_3Cl$: Calcd. (%): C, 59.42; H, 8.25; O, 19.11; N, 7.17; Cl, 6.05. Found (%): C, 59.44; H, 8.22; O, 19.08; N, 7.22; Cl, 6.08.

Ultraviolet absorption spectrum (methanol): $\lambda_{max}$: 213 mμ, 248 mμ and 299 mμ

N[4]-Propionyl-1-β-D-arabinofuranosylcytosine-5'-chloropropionate.

N[4]-Butyryl-1-β-D-arabinofuranosylcytosine-5'-chloropropionate.

N[4]-Valeryl-1-β-D-arabinofuranosylcytosine-5'-chloropropionate.

N[4]-Caproyl-1-β-D-arabinofuranosylcytosine-5'-chloropropionate.

N[4]-Heptanoyl-1-β-D-arabinofuranosylcytosine-5'-chloropropionate.

N[4]-Caprylyl-1-β-D-arabinofuranosylcytosine-5'-chloropropionate.

N[4]-Lauroyl-1-β-D-arabinofuranosylcytosine-5'-chloropropionate.

N[4]-Myristoyl-1-β-D-arabinofuranosylcytosine-5'-chloropropionate.

N[4]-Tetradecenoyl-1-β-D-arabinofuranosylcytosine-5'-chloropropionate.

N[4]-Pentadecanoyl-1-β-D-arabinofuranosylcytosine-5'-chloropropionate.

N[4]-Nonadecanoyl-1-β-D-arabinofuranosylcytosine-5'-chloropropionate.

N[4]-Arachidoyl-1-β-D-arabinofuranosylcytosine-5'-chloropropionate.

N[4]-Behenoyl-1-β-D-arabinofuranosylcytosine-5'-chloropropionate.

N[4]-Lignoceroyl-1-β-D-arabinofuranosylcytosine-5'-chloropropionate.

EXAMPLE 5

3.70 g of diethylamine was added to 0.30 of N[4]-stearoyl-1-β-D-arabinofuranosylcytosine-5'-chloroacetate under an atmosphere of argon followed by stirring for 4 to 5 hours at room temperature. After confirming that the raw material had disappeared by thin layer chromatography, the unreacted diethylamine was distilled off under reduced pressure, i.e., 20 mmHg, under an atmosphere of argon. The powder formed was dissolved in absolute diethyl ether, and diethylamine hydrochloride (which is insoluble in diethyl ether) was filtered out. The diethyl ether was distilled off under reduced pressure, i.e., 20 mmHg, to provide 0.32 g of a white powder, which was then purified by column chromatography using a column of silica gel to give 0.29 g of a white powder (yield, 91 mole%).

Elementary analysis for $C_{33}H_{58}O_7N_4$: Calcd. (%): C, 63.65; H, 9.37; O, 17.98; N, 9.00. Found (%): C, 63.72; H, 9.33; O, 18.00; N, 9.10.

Ultraviolet absorption spectrum (dioxane): $\lambda_{max}$: 248 mμ, and 307 mμ

Infrared absorption spectrum (KBr): 1733 cm$^{-1}$

Nuclear magnetic resonance spectrum δ(ppm) CDCl$_3$:

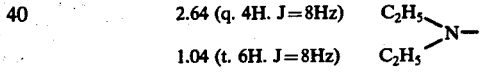

2.64 (q. 4H. J=8Hz)  C$_2$H$_5$\
1.04 (t. 6H. J=8Hz)  C$_2$H$_5$/ N—

EXAMPLE 6

Following the same procedures as described in Example 5 except for varying the starting materials, the following N[4]-acyl-1-β-D-arabinofuranosylcytosine-5'-amino esters were obtained:

N[4]-Palmitoyl-1-β-D-arabinofuranosylcytosine-5'-N,N-diethylglycinate:

Elementary analysis for $C_{31}H_{54}O_7N_4$: Calcd. (%): C, 62.60; H, 9.15; O, 18.83; N, 9.42. Found (%): C, 62.77; H, 9.12; O, 18.77; N, 9.50.

Ultraviolet absorption spectrum (dioxane): 248 mμ and 307 mμ

N[4]-Margaroyl-1-β-D-arabinofuranosylcytosine-5'-N,N-diethylglycinate:

Elementary analysis for $C_{32}H_{56}O_7N_4$: Calcd. (%): C, 63.13; H, 9.27; O, 18.40; N, 9.20. Found (%): C, 63.00; H, 9.25; O, 18.35; N, 9.29.

Ultraviolet absorption spectrum (dioxane): 248 mμ and 307 mμ

N[4]-Stearoyl-1-β-D-arabinofuranosylcytosine-5'-N,N-diethylaminopropionate:

Elementary analysis for $C_{34}H_{60}O_7N_4$: Calcd. (%): C, 64.11; H, 9.50; O, 17.59; N, 8.80. Found (%): C, 64.05; H, 9.53; O, 17.71; N, 8.90.

Ultraviolet absorption spectrum (dioxane): 248 mμ and 307 mμ

N$^4$-Palmitoyl-1-β-D-arabinofuranosylcytosine-5'-N,N-diethylaminopropionate:

Elementary analysis for $C_{32}H_{56}O_7N_4$: Calcd. (%): C, 63.13; H, 9.27; O, 18.40; N, 9.20. Found (%): C, 63.35; H, 9.25; O, 18.29; N, 9.18.

Ultraviolet absorption spectrum (dioxane): 248 mμ and 307 mμ

N$^4$-Margaroyl-1-β-D-arabinofuranosylcytosine-5'-N,N-diethylaminopropionate:

Elementary analysis for $C_{33}H_{58}O_7N_4$: Calcd. (%): C, 63.65; H, 9.37; O, 17.98; N, 9.00. Found (%): C, 63.67; H, 9.42; O, 18.01; N, 9.03.

Ultraviolet absorption spectrum (dioxane): 248 mμ and 307 mμ.

N$^4$-Propionyl-1-β-D-arabinofuranosylcytosine-5'-N,N-diethylglycinate.

N$^4$-Propionyl-1-β-D-arabinofuranosylcytosine-5'-N,N-diethylaminopropionate.

N$^4$-Butyryl-1-β-D-arabinofuranosylcytosine-5'-N,N-diethylglycinate.

N$^4$-Butyryl-1-β-D-arabinofuranosylcytosine-5'-N,N-diethylaminopropionate.

N$^4$-Valeryl-1-β-D-arabinofuranosylcytosine-5'-N,N-diethylglycinate.

N$^4$-Valeryl-1-β-D-arabinofuranosylcytosine-5'-N,N-diethylaminopropionate.

N$^4$-Caproyl-1-β-D-arabinofuranosylcytosine-5'-N,N-diethylglycinate.

N$^4$-Caproyl-1-β-D-arabinofuranosylcytosine-5'-N,N-diethylaminopropionate.

N$^4$-Heptanoyl-1-β-D-arabinofuranosylcytosine-5'-N,N-diethylglycinate.

N$^4$-Heptanoyl-1-β-D-arabinofuranosylcytosine-5'-N,N-diethylaminopropionate.

N$^4$-Caprylyl-1-β-D-arabinofuranosylcytosine-5'-N,N-diethylgylcinate.

N$^4$-Caprylyl-1-β-D-arabinofuranosylcytosine-5'-N,N-diethylaminopropionate.

N$^4$-Lauroyl-1-β-D-arabinofuranosylcytosine-5'-N,N-diethylglycinate.

N$^4$-Lauroyl-1-β-D-arabinofuranosylcytosine-5'-N,N-diethylaminopropionate.

N$^4$-Myristoyl-1-β-D-arabinofuranosylcytosine-5'-N,N-diethylglycinate.

N$^4$-Myristoyl-1-β-D-arabinofuranosylcytosine-5'-N,N-diethylaminopropionate.

N$^4$-Tetradecenoyl-1-β-D-arabinofuranosylcytosine-5'-N,N-diethylglycinate.

N$^4$-Tetradecenoyl-1-β-D-arabinofuranosylcytosine-5'-N,N-diethylaminopropionate.

N$^4$-Pentadecanoyl-1-β-D-arabinofuranosylcytosine-5'-N,N-diethylglycinate.

N$^4$-Pentadecanoyl-1-β-D-arabinofuranosylcytosine-5'-N,N-diethylaminopropionate.

N$^4$-Nonadecanoyl-1-β-D-arabinofuranosylcytosine-5'-N,N-diethylglycinate.

N$^4$-Nonadecanoyl-1-β-D-arabinofuranosylcytosine-5'-N,N-diethylaminopropionate.

N$^4$-Arachidoyl-1-β-D-arabinofuranosylcytosine-5'-N,N-diethylglycinate.

N$^4$-Arachidoyl-1-β-D-arabinofuranosylcytosine-5'-N,N-diethylaminopropionate.

N$^4$-Behenoyl-1-β-D-arabinofuranosylcytosine-5'-N,N-diethylglycinate.

N$^4$-Behenoyl-1-β-D-arabinofuranosylcytosine-5'-N,N-diethylaminopropionate.

N$^4$-Lignoceroyl-1-β-D-arabinofuranosylcytosine-5'-N,N-diethylglycinate.

N$^4$-Lignoceroyl-1-β-D-arabinofuranosylcytosine-5'-N,N-diethylaminopropionate.

DISPERSIBILITY TEST

The dispersibility of the N$^4$-acyl-1-β-D-arabinofuranosylcytosine-5'-amino esters according to this invention was evaluated by adding 10 mg of the test compound to 1 ml of water; the results obtained are shown in Table 1 below.

As is shown in Table 1, the compounds according to the present invention possess increased dispersibility in water as compared with the starting material, N$^4$-acyl-1-β-D-arabinofuranosylcytosine.

Table 1

| N$^4$-acyl group | N$^4$-acyl-1-β-D-arabino-furanosylcytosine | N$^4$-acyl-1-β-D-arabino-furanosylcytosine-5'-N,N-diethylglycinate | N$^4$-acyl-1-β-D-arabino-furanosylcytosine-5'-N,N-diethylamino-propionate |
|---|---|---|---|
| propionyl | dispersed | soluble (10 mg/ml) | soluble (10 mg/ml) |
| butyryl | " | soluble ( 5 mg/ml) | soluble ( 5 mg/ml) |
| valeryl | floating on surface of water | extremely well dispersed | extremely well dispersed |
| caproyl | " | " | " |
| heptanoyl | " | " | " |
| caprylyl | " | " | " |
| lauroyl | " | " | " |
| myristoyl | " | " | " |
| tetradecenoyl | " | " | " |
| pentadecanoyl | " | " | " |
| palmitoyl | " | " | " |
| margaroyl | " | " | " |
| stearoyl | " | " | " |
| nonadecanoyl | " | " | " |
| arachidoyl | " | " | " |
| behenoyl | " | " | " |

BIOLOGICAL TEST

The anti-cancer activity of the novel compounds, N$^4$-acyl-1-β-D-arabinofuranosylcytosine-5'-amino esters, according to the present invention was determined as follows: 100,00 cells/mouse of L-1210 leukemia were administered by intraperitoneal injection to groups of CDF$_1$ male mice (3 mice per group), and, after 2 days and after 6 days, a physiological saline solution containing the test material in an amount of 100, 200 or 400 mg/Kg was administered by intraperitoneal injection to the mice. Further, a physiological saline solution containing no test material was similarly administered to the mice infected with L-1210 leukemia for comparison purposes.

The anti-cancer activity of the test material was evaluated by means of survival rate comparison, T/C (%), that is, 100 times the mean survival period of the groups injected with the test material divided by the mean survival period of the comparison groups which were not injected with the test material.

According to this evaluation, a survival rate comparison, T/C (%), of lower than 100% indicates that the test material is toxic, and one of higher than 125% indicates that the test material possesses therapeutic effects. As will be seen from the results given in Table 2 below, among the compounds of this invention, those wherein the $N^4$-acyl group has 14 to 22 carbon atoms exhibited a high survival rate at a low concentration, and, therefore, are particularly useful.

Table 2

| $N^4$-acyl group | $N^4$-acyl-1-β-D-arabino-furanosylcytosine-5'-N,N-diethylglycinate T/C (%) | | | $N^4$-acyl-1-β-D-arabino-furanosylcytosine-5'-N,N-diethylaminopropionate T/C (%) | | |
|---|---|---|---|---|---|---|
| | 400 (mg/Kg) | 200 (mg/Kg) | 100 (mg/Kg) | 400 (mg/Kg) | 200 (mg/Kg) | 100 (mg/Kg) |
| propionyl | 130 | 125 | 125 | 128 | 120 | 120 |
| butyryl | 132 | 127 | 127 | 132 | 125 | 120 |
| valeryl | 132 | 130 | 127 | 130 | 130 | 119 |
| caproyl | 140 | 133 | 125 | 133 | 123 | 125 |
| heptanoyl | 143 | 127 | 123 | 141 | 132 | 127 |
| caprylyl | 200 | 182 | 140 | 202 | 181 | 135 |
| lauroyl | 225 | 201 | 170 | 212 | 173 | 141 |
| myristoyl | 90 | 192 | 278 | 93 | 182 | 281 |
| tetradecenoyl | 91 | 309 | 250 | 99 | 288 | 230 |
| pentadecanoyl | 95 | 305 | 320 | 95 | 310 | 340 |
| palmitoyl | 99 | 280 | 349 | 125 | 340 | 381 |
| margaroyl | 120 | 279 | 390 | 111 | 321 | 388 |
| stearoyl | 140 | 244 | 355 | 140 | 315 | 344 |
| nonadecanoyl | 120 | 260 | 298 | 120 | 280 | 295 |
| arachidoyl | 303 | 362 | 300 | 311 | 351 | 299 |
| behenoyl | 341 | 298 | 260 | 321 | 288 | 250 |
| lignoceroyl | 120 | 125 | 127 | 115 | 127 | 131 |
| 1-β-D-arabino-furanosylcytosine | | | | 150 | 130 | 110 |

While the invention has been described in detail and with reference to specific embodiments thereof, it will be apparent to one skilled in the art that various changes and modifications can be made therein without departing from the spirit and scope thereof.

What is claimed is:

1. A nucleoside derivative represented by the formula:

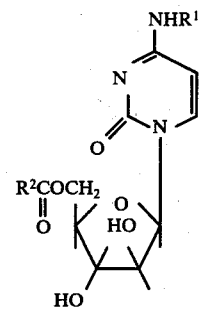

wherein $R^1$ represents an acyl group having 3 to 28 carbon atoms and $R^2$ represents an $XCH_2$-, $XCH_2CH_2$— or $CH_3CHX$-group, wherein X represents chloro, bromo, a $(CH_3)_2N$-group or a $(C_2H_5)_2N$-group.

2. A nucleoside derivative represented by the formula:

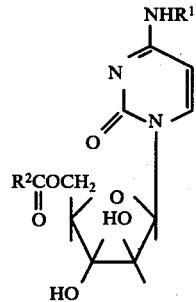

wherein $R^1$ represents an acyl group having 14 to 22 carbon atoms and $R^2$ represents an $XCH_2$—, $XCH_2CH_2$— or $CH_3CHX$-group, wherein X represents chloro, bromo, a $(CH_3)_2N$-group or a $(C_2H_5)_2N$-group.

3. The nucleoside derivative as claimed in claim 2, wherein said acyl group is myristoyl, tetradecenoyl, pentadecanoyl, palmitoyl, margaroyl, stearoyl, nonadecanoyl, arachiodoyl or behenoyl.

4. The nucleoside derivative as claimed in claim 1, wherein said X represents a $(CH_3)_2N$-group or a $(C_2H_5)_2N$-group.

5. The nucleoside derivative as claimed in claim 4, wherein said acyl group is myristoyl, tetradecenoyl pentadecanoyl, palmitoyl, margaroyl, stearoyl, nonadecanoyl, arachiodoyl or behenoyl.

* * * * *